United States Patent
Fahmi et al.

(10) Patent No.: US 10,769,785 B2
(45) Date of Patent: Sep. 8, 2020

(54) NEURAL NETWORK FOR NEURODEGENERATIVE DISEASE CLASSIFICATION

(71) Applicant: Siemens Medical Solutions USA, Inc., Malvern, PA (US)

(72) Inventors: Rachid Fahmi, Knoxville, TN (US); Sven Zuehlsdorff, Knoxville, TN (US); Ludovic Sibille, Didcot (GB)

(73) Assignee: Siemens Medical Solutions USA, Inc., Malvern, PA (US)

( * ) Notice: Subject to any disclaimer, the term of this patent is extended or adjusted under 35 U.S.C. 154(b) by 148 days.

(21) Appl. No.: 16/238,696

(22) Filed: Jan. 3, 2019

(65) Prior Publication Data

US 2020/0090326 A1 Mar. 19, 2020

Related U.S. Application Data (60) Provisional application No. 62/731,134, filed on Sep. 14, 2018.

(51) Int. Cl.
*G06T 7/00* (2017.01)
*G06T 7/11* (2017.01)

(52) U.S. Cl.
CPC .............. *G06T 7/0012* (2013.01); *G06T 7/11* (2017.01); *G06T 2207/10104* (2013.01); *G06T 2207/10108* (2013.01); *G06T 2207/20081* (2013.01); *G06T 2207/20084* (2013.01); *G06T 2207/20132* (2013.01); *G06T 2207/30016* (2013.01)

(58) Field of Classification Search
USPC ........................ 382/128, 131; 706/15, 25, 41
See application file for complete search history.

(56) References Cited

U.S. PATENT DOCUMENTS

| | | | |
|---|---|---|---|
| 2010/0183202 A1* | 7/2010 | Takahashi | A61B 6/037 382/128 |
| 2011/0160543 A1* | 6/2011 | Parsey | A61B 6/501 600/300 |
| 2014/0119627 A1* | 5/2014 | Skretting | G06T 7/0016 382/131 |
| 2014/0350380 A1* | 11/2014 | Eidelberg | A61B 6/037 600/410 |
| 2016/0260216 A1* | 9/2016 | Wu | A61B 6/5205 |
| 2016/0300352 A1* | 10/2016 | Raj | G06T 7/0012 |

(Continued)

OTHER PUBLICATIONS

Coregistration and Spatial Normalisation, https://www.fil.ion.ucl.ac.uk/mfd_archive/2009/Spatial.ppt visted Dec. 3, 2018.

(Continued)

*Primary Examiner* — Ishrat I Sherali (57) ABSTRACT

A method for configuring a neural network comprises: accessing a plurality of three-dimensional (3D) emission image data sets collected by an emission scanner from respective brains of respective subjects; transforming each of the plurality of 3D emission image data sets to a respective two-dimensional (2D) image; cropping portions of each respective 2D image to remove image data corresponding to tissue outside of a striatum of each of the respective brains, to form respective cropped 2D striatum images; and training a neural network to detect a presence of a Parkinsonian syndrome using the cropped 2D striatum images.

20 Claims, 5 Drawing Sheets

(56) References Cited

U.S. PATENT DOCUMENTS

| | | | | |
|---|---|---|---|---|
| 2017/0251985 | A1* | 9/2017 | Howard | A61B 5/11 |
| 2018/0204327 | A1* | 7/2018 | Matthews | A61B 5/4842 |
| 2019/0200893 | A1* | 7/2019 | Grouchy | A61B 5/726 |
| 2019/0328909 | A1* | 10/2019 | Jones | G16H 50/30 |

OTHER PUBLICATIONS

Wu, Ping et al., "Deep Learning on 18F-FDG PET Imaging for Differential Diagnosis of Parkinsonian Syndromes" J. Nucl. Med., May 1, 2018, vol. 59, No. supplement 1 624, pp. 1-3.

Choi, Hongyoon et al., "Refining diagnosis of PArkinson's disease with deep learning-based interpretation of dopamine transporter imaging" Neuroimage Clin. Sep. 10, 2017, 16, pp. 586-594.

* cited by examiner

NEURAL NETWORK FOR NEURODEGENERATIVE DISEASE CLASSIFICATION

RELATED APPLICATION

The present patent document claims the benefit of the filing date under 35 U.S.C. § 119(e) of Provisional U.S. Patent Application Ser. No. 62/731,134, filed Sep. 14, 2018, which is hereby incorporated by reference.

FIELD

This disclosure relates to medical imaging generally, and more specifically to using emission imagery techniques for Parkinsonian syndrome classification.

BACKGROUND

Emission images (Single-photon emission computerized tomography (SPECT) images or positron emission tomography (PET) images) of subjects injected with a tracer targeting the dopaminergic system (such as DaTscan® $^{123}$I-Ioflupane SPECT tracer sold by GE Healthcare of Arlington Heights, Ill.) have been either interpreted visually or by combining visual observation and semi-quantitative analysis. Quantification involves (manual or automatic) placement of regions of interest over the striatum and computing uptake ratios with respect to a background region, and the left-right asymmetries with respect to uptake. Quantification has been shown to increase inter-reader agreement and the reporting confidence, and to reduce the number of equivocal cases. Due to age-dependence of DaTscan® tracer uptake, comparisons to age-matched reference values are of most help in resolving challenging cases (e.g., borderline or early disease cases).

A convolutional neural network (CNN) can be trained to perform classification for Parkinsonian Syndromes (PSs). For example, Wu et al., "Deep Learning on $^{18}$F-FDG PET Imaging for Differential Diagnosis of Parkinsonian Syndromes," J Nucl Med, vol. 59, No. supplement 1, p 624, May 1, 2018, describes a method to compress three-dimensional (3D) imaging data into two-dimensional (2D) data and use the 2D data to train CNNs for differential diagnosis of Parkinsonism using 18F-Fluorodeoxyglucose ($^{18}$F-FDG) PET brain images.

SUMMARY

In some embodiments, a method for configuring a neural network comprises: accessing a plurality of three-dimensional (3D) emission image data sets collected by an emission scanner from respective brains of respective subjects; transforming each of the plurality of 3D emission image data sets to a respective two-dimensional (2D) image; cropping portions of each respective 2D image to remove image data corresponding to tissue outside of a striatum of each of the respective brains, to form respective cropped 2D striatum images; and training a neural network to detect a presence of a Parkinsonian syndrome using the cropped 2D striatum images.

In some embodiments, a system for configuring a neural network comprises a processor coupled to access a plurality of three-dimensional (3D) emission image data sets collected by an emission scanner from respective brains of respective subjects. The processor is configured to transform each of the plurality of 3D emission image data sets to a respective two-dimensional (2D) image. The processor is configured to crop portions of each respective 2D image to remove image data corresponding to tissue outside of a striatum of each of the respective brains, to form respective cropped 2D striatum images. A neural network is configured to receive the cropped 2D striatum images for training the neural network to detect a presence of a Parkinsonian syndrome using the cropped 2D striatum images.

In some embodiments, a non-transitory, machine readable storage medium is encoded with program instructions, such that when a processor executes the program instructions, the program instructions configure the processor to perform a method for configuring a neural network, comprising: accessing a plurality of three-dimensional (3D) emission image data sets collected by an emission scanner from respective brains of respective subjects; transforming each of the plurality of 3D emission image data sets to a respective two-dimensional (2D) image; cropping portions of each respective 2D image to remove image data corresponding to tissue outside of a striatum of each of the respective brains, to form respective cropped 2D striatum images; and training a neural network to detect a presence of a Parkinsonian syndrome using the cropped 2D striatum images.

DETAILED DESCRIPTION

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation.

Parkinsonian syndromes (including Parkinson's disease (PD), Multiple system atrophy (MSA) and progressive supranuclear palsy (PSP)) are primarily characterized by dysfunction of the presynaptic dopaminergic system which can be analyzed at the striatal level using dopamine transporter imaging with a dopaminergic radioligand, such as, for example, $^{123}$I-ioflupane ("DATSCAN®" brand $^{123}$I-ioflupane, a single-photon emission computerized tomography (SPECT) tracer sold by GE Healthcare Limited of Buckinghamshire, UK). In some embodiments, these images are interpreted either visually or combining visual interpretation with a semi-quantitative analysis approach which may use comparisons of quantified parameters to age-matched reference values when available. Some embodiments described herein use a deep learning-based approach for interpretation of dopamine transporter (DAT) images in patients with PD.

Systems and method described herein can reduce the computational effort to train a convolutional neural network (CNN) designed for disease classification using images acquired with tracers targeting the dopaminergic system. For example, dopamine transporter imaging with "DATSCAN®" brand $^{123}$I-FP-CIT SPECT tracer (sold by GE Healthcare Limited of Buckinghamshire, UK) can be used to assess dopamine degeneration in patients with a Parkinsonian syndrome. Some embodiments employ deep learning (DL) to assess DAT images, e.g., for classification purposes. This disclosure describes a pre-processing method that captures intrinsic uptake information in volumetric DAT data, or data acquired with any PET or SPECT dopaminergic radioligand, in a compressed 2D presentation for faster training and convergence of the DL network used.

Some embodiments pre-process training image data for a classifier that classifies static input image data as corresponding to a healthy brain or a Parkinson's disease (PD) brain. The static input data can be single-photon emission computerized tomography (SPECT) image data or static positron emission tomography (PET) image data, collected by a SPECT or PET scanner, respectively.

The resulting training data set includes a compressed (2D) image, which is cropped, so a large fraction (e.g., 10% or more) of the pixels in the cropped 2D image correspond to the striatum. For example, brains of PD patients are distinguishable by reduced DAT tracer uptake within the striatum, compared to the brain of a healthy patient. By substantially limiting the training data to striatum tissues, the CNN can be trained to classify brains according to the relevant tracer uptake in the striatum, and avoid learning of immaterial differences among the brain tissue outside of the striatum. The size of the training data set can be reduced, and training can be performed more quickly, with reduced computing resources.

Figure 1:
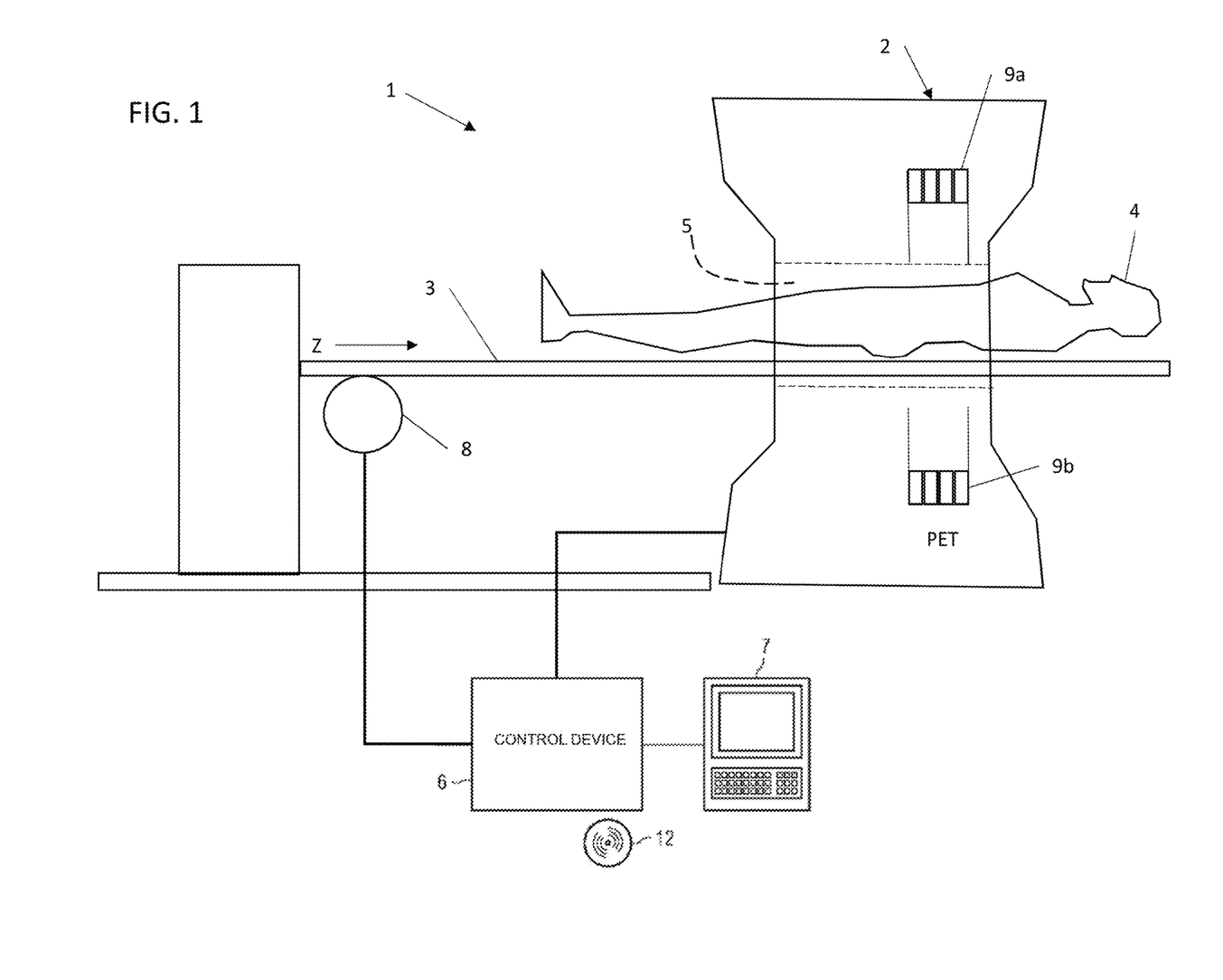
FIG. 1 is a schematic diagram of a medical imaging system according to some embodiments.
Figure 3:
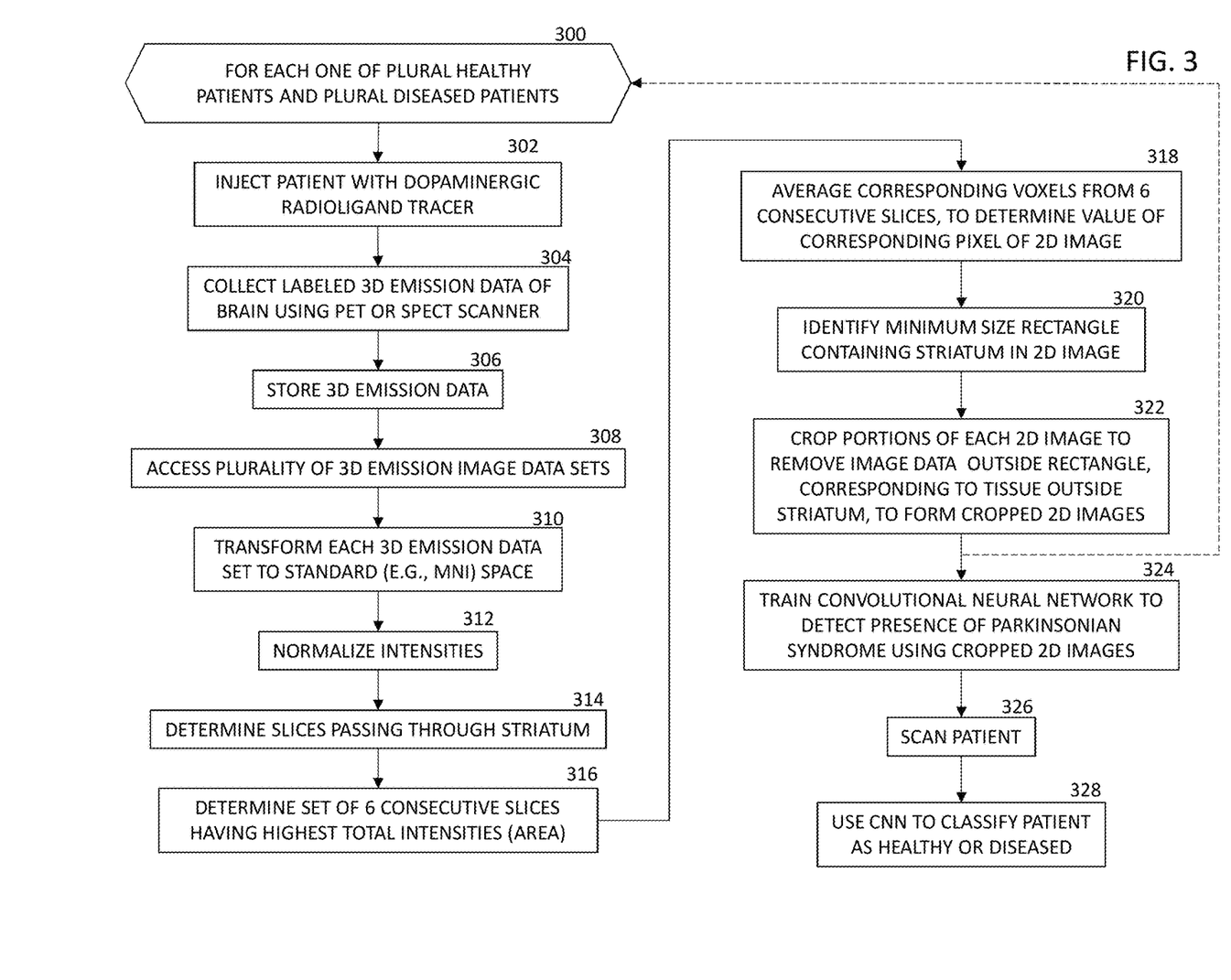
FIG. 3 is a flow chart of an embodiment of a method.

FIG. 1 shows a schematic diagram of a medical imaging system 1. In some embodiments, the system 1 includes an activity (emission) image scanner 2. The activity (emission) image scanner 2 can be a positron emission tomography (PET) scanner or a single-photon emission computerized tomography (SPECT) scanner. The system 1 comprises: an examination table 3 for a patient 4 who can be moved on the examination table 3 through an opening 5 of the scanner 2, a control device 6, a processor 7 and a drive unit 8. The control device 6 activates the scanner 2 and receives (from the scanner 2) signals which are picked up by the scanner 2. With the aid of the scanner 2, gamma radiation can be collected (if scanner 2 is a PET scanner or a SPECT scanner). Also disposed in the scanner 2 is a ring of detector blocks 9a, 9b (collectively referred to as 9) for acquiring photons which are created by annihilation of electrons and positrons in the detector blocks 9a, 9b. Although only 2 detector blocks 9a, 9b are shown in FIG. 3 for ease of viewing, scanner 2 can have many detector blocks 9 arranged in a cylinder around the circumference of the scanner 2. The control device 6 is further operable to receive signals from the detector blocks 9a, 9b and is capable of evaluating these signals for creating PET or SPECT images. The control device 6 further activates the drive unit 8 in order to move the examination table 3 in a direction Z together with the patient 4 through the opening 5 of the scanner 2. The control device 6 and the processor 7 can, for example, comprise a computer system with a screen, a keyboard and a non-transitory, machine readable storage medium 12 (hereinafter, "storage medium") on which electronically-readable control information is stored, which is embodied so that it carries out the method described below when the storage medium 12 is used in conjunction with the processor 7 and the control device 6.

Figure 2:
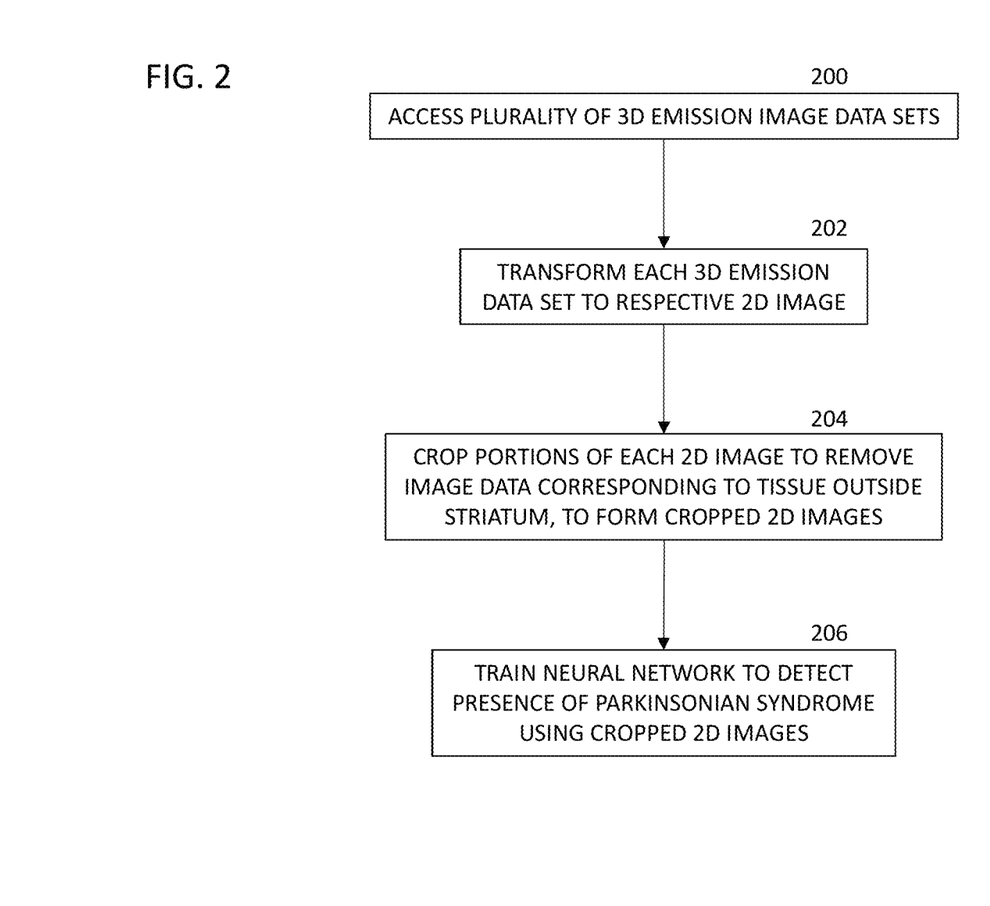
FIG. 2 is a flow chart of an exemplary method according to some embodiments.

FIG. 2 is a flow chart of an example of a method, in which the pre-processing compresses the acquired 3D brain SPECT or PET scan into a 2D patch encompassing the striatum as follows:

At step 200, the processor accesses a plurality of 3D emission image data sets corresponding to SPECT images or static PET images. Each 3D emission image data set corresponds to a plurality of slices. Each slice corresponds to a respective array of voxels arranged between a respective pair of parallel planes (e.g., planes spaced 2 mm apart) passing through the brain. The 3D emission image data sets can include newly collected image data from a SPECT or PET scanner 2, previously collected image data stored in a non-transitory, machine-readable storage medium 12, or a combination of the two.

At step 202, each of the plurality of 3D emission image data sets are transformed to a respective two-dimensional (2D) image.

At step 204, portions of each respective 2D image are cropped to remove image data corresponding to tissue outside of a striatum of each of the respective brains, to form respective cropped 2D striatum images. For example, the 2D image can be a rectangle containing the striatum. In some embodiments, since all images are normalized to a standard space, the same rectangle size (in the standard space) is used to automatically crop area around the striatum for all training/testing data. In some examples, the edges of the rectangles of the 2D images do not extend beyond the striatum, so that each side of the rectangles are tangent to the boundary of the striatum. In other examples, the edges of the rectangles of the 2D images extend by a small constant distance (e.g. a distance of approximately a width dimension of the striatum) beyond the boundary of the striatum. In some examples, the striatum constitutes at least 10% of the area of the cropped 2D image. In some embodiments, the striatum constitutes 10% to 50% of the area of the cropped 2D image.

At step 206, a neural network is trained to detect a presence of a Parkinsonian syndrome using the cropped 2D striatum images. Because the cropped 2D striatum images reduce or minimize the number of pixels corresponding to brain tissue outside of the striatum, the amount of irrelevant information in the input training dataset is minimized. The CNN trained using the cropped 2D striatum images can classify healthy versus PD brains with greater accuracy, and training can be accomplished more quickly.

Figure 4:
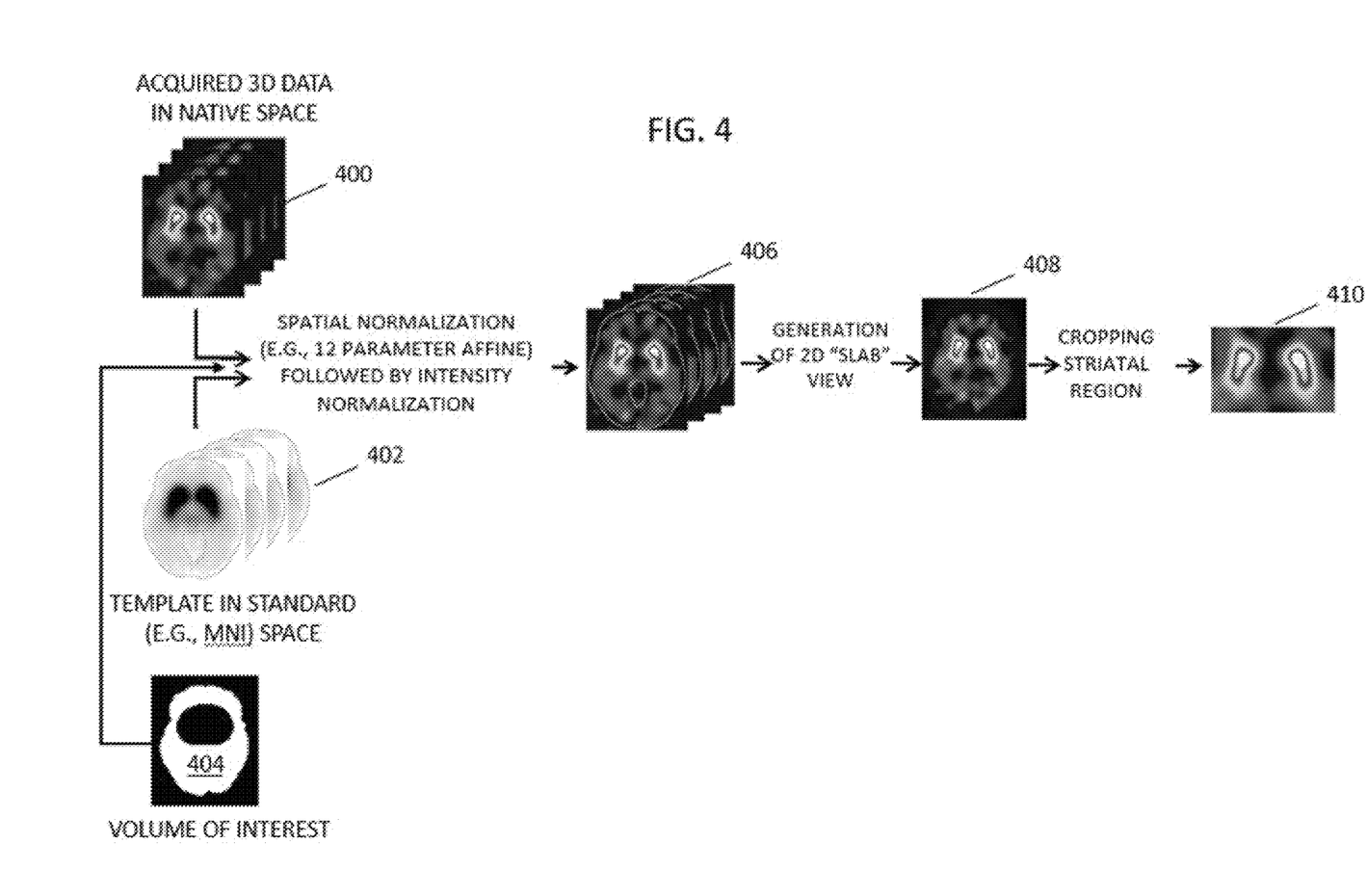
FIG. 4 is a schematic diagram showing the pre-processing of three-dimensional emission image data to provide a training data set for a classifying images from SPECT or PET scanner.

FIG. 3 is a flow chart of an example of a method according to some embodiments. FIG. 4 is a schematic diagram illustrating the training images generated by the pre-processing method of FIG. 3.

At step 300 of FIG. 3, a loop containing steps 302-322 is performed for each of a plurality of patients, including a plurality of healthy patients and a plurality of patients having a Parkinsonian syndrome affecting dopamine transporter uptake by the striatum.

At step 302, a patient is injected with a dopaminergic radioligand tracer, such as $^{123}$I-ioflupane. In various embodiments, the tracer may be [$^{123}$I]FP-CIT, [$^{123}$I]β-CIT, [$^{99m}$Tc]TRODAT-1, [$^{123}$I]PE2I, [$^{123}$I]-altropane, [$^{123}$I]IBZM, [$^{18}$F]dopa, [$^{11}$C]dopa, [$^{11}$C]cocaine, [$^{3}$H]WIN, [$^{11}$C]altropane, [$^{11}$C]/[$^{18}$F]β-CFT, [$^{11}$C]FE-CIT, [$^{11}$C]dMP, [$^{11}$C]DTBZ, [$^{11}$C]raclopride, [$^{18}$F]DMFP, or [$^{11}$C]NMSP.

At step 304, the scanner 2 collects 3D emission data (400, FIG. 4) of the patient's brain in the native space of the PET or SPECT scanner. The data are used to reconstruct static PET or SPECT images (e.g., standard uptake value (SUV) images). The static PET or SPECT images are reviewed (e.g., manually reviewed), and the 3D emission data are labeled as healthy control (HC) or Parkinsonian syndrome (e.g., Parkinson's Disease (PD), Multiple system atrophy (MSA), or progressive supranuclear palsy (PSP)). While performing the manual review, the clinician can consider previous diagnoses, comparisons to reference binding ratios and asymmetries, and other available information.

At step 306, the labeled 3D emission training data are stored in a non-transitory, machine-readable storage medium.

At step 308, the plurality of 3D emission data sets are accessed.

At step 310, the original 3D emission images are spatially normalized to a standard space, such as the standard Montreal Neurological Institute (MM), space. This step resamples the 3D image into a standard resolution (e.g., a 2×2×2 mm$^3$ resolution).

For example, in some embodiments, a 12 parameter affine transform is used. The transform fits a standard brain template (402, FIG. 4) to the 3D emission images (400, FIG. 4) by a combination of three translations, three rotations, three zooms, and three shears. The affine registration matches positions and sizes of images, where the three translations and three rotations achieve a standard location, and the three zooms and three shears register brains of different shapes and sizes.

At step 312, voxel intensities of the spatially normalized 3D image are normalized by dividing them by the mean intensity in a volume of interest (404, FIG. 4) comprised, for example, of "whole brain minus striatum". Thus, the uptake values within the striatum, for each person, are expressed relative to the average brain uptake intensity outside the striatum for that person. The normalized 3D images 406 are shown in FIG. 4.

At step 314, the slices of the 3D image data passing through the striatum are determined. This determination is facilitated by having the 3D image data in the MNI space.

Steps 316 and 318 provide an example defining a 2D image in which each pixel is an average of the corresponding voxel locations of a subset of the slices corresponding to the striatum. In this example, the 2D pixel values are (arithmetic) mean values in a 12 mm volume passing through the striatum.

At step 316 a subset of slices are identified, including a predetermined number of consecutive transverse slices of the brain passing through the striatum. For example, in some embodiments, signal intensity profiles of the slices that overlap with the striatum cavity are calculated. From these slices, six consecutive slices are selected so that the total signal intensity is maximized (i.e. those slices have the maximum portion of the intensity profile in the slice direction). The six slices are then averaged to form the 2D "slab view" image (408, FIG. 4) of the brain.

For example, assume each slice is 2 mm wide, and six consecutive slices (totaling 12 mm) are identified. Each possible subset of slices passing through the striatum and containing six consecutive slices (12 mm total slab thickness) is identified. The number of candidate subsets is the total number of slices minus the number of consecutive slices in each subset, plus one. For each subset, a total (or average) of the intensity values for each voxel is determined, and the subset having the greatest total (or average) is selected. This subset (12 mm slab) has the highest peak distribution volume ratio.

At step 318, the selected six consecutive slices are then averaged to form the 2D image values. In some embodiments, the averages are calculated by arithmetic mean. The value of each pixel of the 2D image is the average of the corresponding six voxels in the six consecutive slices of the 3D image.

At step 320, a minimum-size rectangle containing the striatum in the 2D image is identified. In some embodiments, the minimum-size rectangle does not extend beyond the striatum on any side. In other embodiments, the minimum-size rectangle extends beyond the striatum by a predetermined distance on each side.

At step 322, the 2D image is cropped to delete portions of the 2D image outside of the striatum. In some embodiments, a narrow frame or border of brain tissue is kept around the striatum (e.g., having a width about the size of one side of the striatum) for CNN training. For example, a frame of brain tissue around the striatum, having a width about the size of one side of the striatum, can be kept. FIG. 4 shows the cropped 2D image 410 of the striatum. The exemplary 2D image 410 shows a healthy striatum, with the two "comma-shaped" segments approximately equal in size (corresponding to approximately equal dopamine transporter uptake). The white, comma shaped regions indicate the highest dopamine transporter uptake values.

At step 324, a training data set containing the plurality of cropped 2D images is used to train a neural network, such as a CNN, to classify images of patients' brains. The cropped 2D images allow rapid training for at least two reasons. First, the cropped 2D images are smaller than the original full 3D image data sets, so computation time per image is reduced. Second, a large fraction of the cropped 2D images contain relevant striatum dopamine transporter uptake information, and a smaller fraction of the cropped 2D images contains irrelevant information related to dopamine transporter uptake in brain tissue outside of the striatum.

At step 326, the scanner is used to scan a patient's brain in the clinical phase.

At step 328, the trained CNN is used to classify the patient as being healthy or diseased (with a Parkinsonian syndrome).

Although the example of FIG. 3 uses six consecutive 2-mm slices, other embodiments can use different numbers of slices in the "slab" and/or different slice thickness.

FIG. 4 schematically shows the pre-processing of the image data. Inputs to the pre-processing include acquired 3D emission image data 400 in the native space of the scanner, a brain template 402 in a standard space (e.g., MNI space), and a mask defining a volume of interest. The input data are spatially normalized, followed by intensity scaling, resulting in normalized 3D image data 406. A predetermined number (e.g., 6) of slices of the 3D image data passing through the striatum and having the highest intensity value are selected. The positionally corresponding voxels of the selected slices are averaged to form a 2D "slab view" image 408. The 2D image 408 is cropped to remove pixels outside the striatum and keep the pixels containing the striatum, resulting in the cropped 2D striatum image 410.

Figure 5:
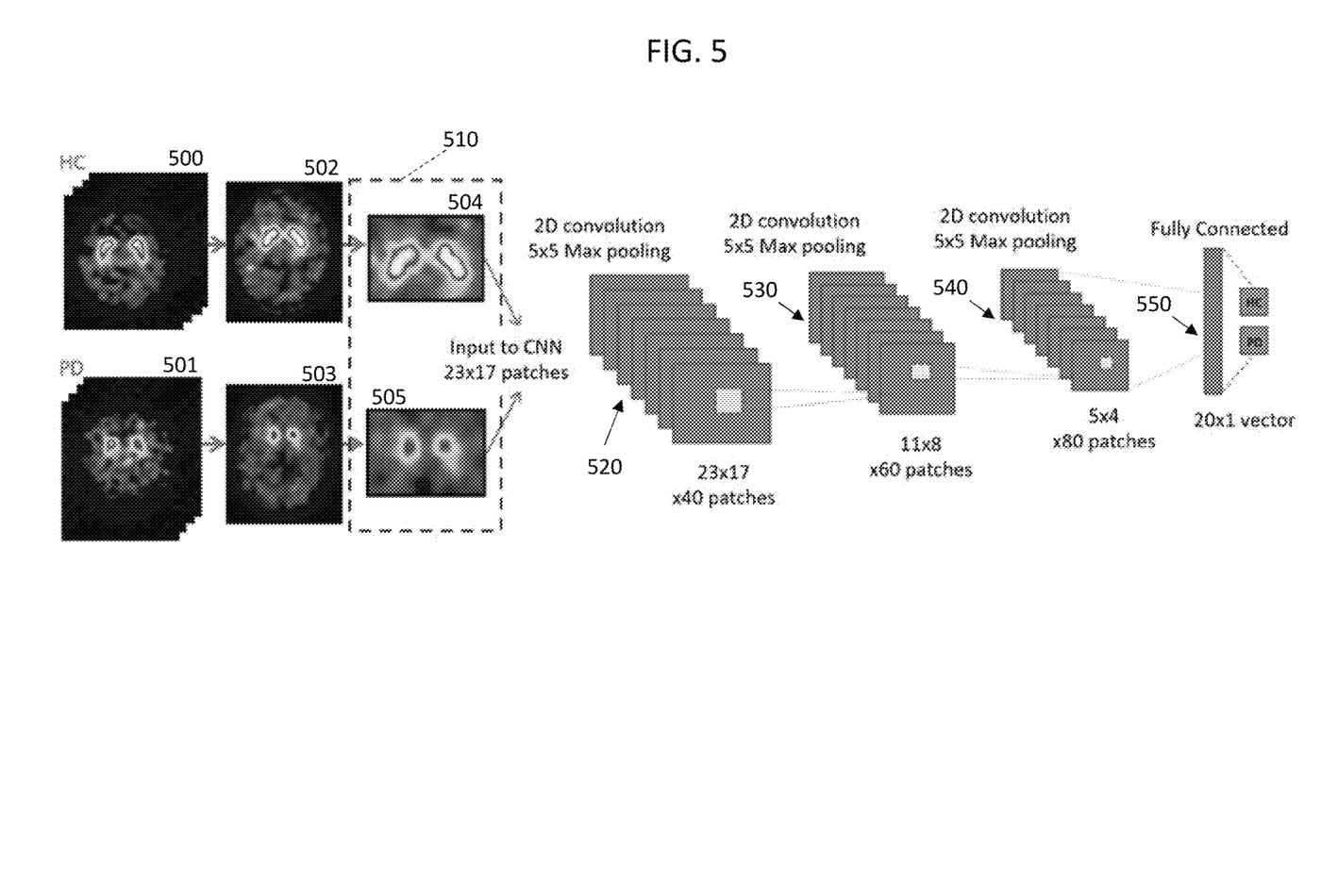
FIG. 5 is a schematic diagram showing a convolutional neural network for classifying the pre-processed images.

FIG. 5 is a schematic diagram of an exemplary deep learning neural network design implemented as a CNN for pre-processing the training data.

The input images include labeled full-brain, 3D SPECT and/or 3D static PET images. The 3D SPECT and/or 3D static PET images include images 500 of healthy control (HC) patient brains and images 501 of Parkinsonian syndrome (PD) patient brains.

For each patient, the system performs spatial normalization to a standard space (e.g., registered to a SPECT template in MM space), and intensity scaling (dividing each voxel value by the average uptake within the volume of interest 404 to create a distribution volume ratio (DVR) image with respect to the "whole brain minus striatum" volume of interest 404). Following the spatial normalization and intensity scaling, a slab comprising six consecutive transverse slices through the striatum having the highest peak DVR, is selected. Corresponding voxels in each of the six slices are averaged to create a 2D DVR image 502, 503. The HC patient brains are represented by images 502, and the PD patient brains are represented by the 2D images 503.

Each of the 2D brain images is cropped to provide a rectangular region of the 2D image around the striatum. The cropping removes data corresponding to portions of the brain outside the striatum. The resulting training data set 510 includes cropped 2D images 504 of HC patient striata, and cropped 2D images 505 of PD patient striata. In the example, the cropped 2D images comprise 40 patches, each patch 23×17 pixels.

The exemplary HC striatum image 504 shows a symmetrical (with respect to the midline of the brain) pair of comma-shaped regions, each having a substantial white area indicating high dopamine transporter uptake. In comparison, the PD striatum image 505 shows an asymmetrical pair of striatal uptake. Uptake in both of the striatum regions in image 505 is reduced relative to the uptake in striatal regions in image 504. Moreover, in the example of FIG. 5, the right striatum region in image 505 is visibly smaller than the left striatum region in image 505. Also, both striatum regions in image 505 lack a white high intensity center region, indicating an overall reduction in dopamine transporter uptake in the PD striatum image 505. The striatum regions in image 505 show reduced uptake in the putamen.

The exemplary CNN has a first convolutional layer 520 for performing a convolution (cross-correlation) with 5×5 tiling, using max pooling (using the maximum value from each of a cluster of neurons at the prior layer). Within convolution layer 520, each filter (not shown) is convolved across the width and height of the input dataset, computing the dot product between the entries of the filter and the input and producing an activation map of that filter. The first convolutional layer 520 outputs (for each cropped 2D image) 60 patches, each 11×8 pixels.

The second convolutional layer 530 performs a convolution with 5×5 tiling, using max pooling. Within second convolution layer 530, each filter (not shown) is convolved across the width and height of the input dataset. The second convolutional layer 530 outputs (for each image) 80 patches, each 5×4 pixels.

The third convolutional layer 540 performs a convolution with 5×5 tiling, using max pooling. Within third convolution layer 540, each filter (not shown) is convolved across the width and height of the input dataset. The third convolutional layer 540 outputs (for each image) 80 patches, each 5×4 pixels.

The high-level reasoning in the CNN is done via a fully connected layer 550. Neurons in the fully connected layer 550 have connections to all activations in the third convolutional layer 540.

The CNN shown in FIG. 5 is only exemplary and does not limit the design of neural networks that can be used for processing the 3D SPECT or PET data to classify patients as healthy or having a Parkinsonian syndrome. For example, the 5×5 convolutions can be replaced by N×N convolutions, where N is any integer. Other types of deep learning networks can be used.

EXAMPLE

"DATSCAN®" images of 176 healthy controls (HC) and 390 PD subjects from the Parkinson's Progression Markers Initiative (PPMI) database (available at www.ppmi-info.org) were used to train and validate a convolutional neural network (CNN) as shown in FIG. 5 to refine image interpretation. In one example, the network was designed to distinguish between "DATSCAN®" images of HC and PD subjects. Summed 2D semi-quantitative images around the basal ganglia were used through a 10-fold cross-validation to evaluate the network. No data augmentation was performed.

For each subject, the reconstructed "DATSCAN®" image was affine-registered with a "DATSCAN®" template in the standard anatomical Montreal Neurological Institute (MNI) space, and scaled voxel by voxel to the mean uptake in the entire brain without striata (volume of interest 404), resulting in a distribution volume ratio (DVR) image. Subsequently, a 12-mm-thick transversal slab centered (in the axial direction) at the striatum in the template space was extracted and averaged to create a 2D DVR-image. Finally, a rectangular mask encompassing the striata in the MNI space was applied to crop a 47×34 DVR patch which was used as input to the network. The CNN was tested using as ground truth the "gold standard diagnosis" of the PPMI cohort.

In addition, Striatal Analysis software (syngo.via, Siemens-Medical-Solutions, USA, Inc., Molecular Imaging, Knoxville, Tenn.) was used to generate a database of normal or reference regional binding ratios from 101 HC subjects (which constituted part of the same set used to train the CNN).

The CNN and the normal database were both used to classify new PPMI data (59 HC and 87 PD, none of which were used to train the CNN or to build the normal database). Although the correct classifications of the new PPMI data were known, the new PPMI data were input to the CNN and compared to normal database as unlabeled data. The performance accuracies of the two approaches (normal DB and exemplary CNN) in classifying the 146 test subjects were compared.

Using the database of quantitative reference values, optimal classification accuracy (CA) using Youden index and area under (receiver-operating-characteristic) curve (AUC) were as follows depending on the striatal region (putamen, caudate, or striatum) chosen for comparison: putamen (CA=92%, AUC=0, 96), caudate (CA=77%, AUC=0.92), and striatum (CA=87%, AUC=0.93). More accurate classifications were achieved using the exemplary CNN (CA=96.5%, AUC=0.986). That is, using the CNN, 96.5% of the diagnoses by the trained CNN matched the correct diagnosis of the PPMI test data.

A network as described herein can potentially assist in resolving inter-observer variability of visual reads of DAT images and substituting a normal database of binding ratios for meaningful clinical quantification of dopamine transporter availability.

In an alternative embodiment, only one slice through the striatum is used as the 2D image, instead of populating each pixel of the 2D image with an average of the corresponding voxels in six slices. For example, the slice having the highest peak DAT uptake intensity, in the striatal cavity area, can be used. Selecting the slice with highest peak intensity transforms each of the plurality of 3D emission image data sets to a respective two-dimensional (2D) image.

Other applications are possible with the emergence of DL approaches, including but not limited to: Assisted interpretation of DaTscan (and other striatal) images (HC vs. PD vs. SWEDD); Differential diagnosis of Parkinsonian syndromes (e.g. PD, PSP, MSA, CBD); or Prediction/monitoring of disease progression and treatment.

Advantages of the exemplary methods include the certainty of extracting and using the most relevant information in the data and better performance and accuracy of a designed deep CNN.

The methods and system described herein may be at least partially embodied in the form of computer-implemented processes and apparatus for practicing those processes. The disclosed methods may also be at least partially embodied in the form of tangible, non-transitory machine readable storage media encoded with computer program code. The media may include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods may also be at least partially embodied in the form of a computer into which computer program code is loaded and/or executed, such that, the computer becomes a special purpose computer for practicing the methods. When implemented on a general-purpose processor, the computer program code segments configure the processor to create specific logic circuits. The methods may alternatively be at least partially embodied in a digital signal processor formed of application specific integrated circuits for performing the methods.

Although the subject matter has been described in terms of exemplary embodiments, it is not limited thereto. Rather, the appended claims should be construed broadly, to include other variants and embodiments, which may be made by those skilled in the art.

What is claimed is:

1. A method for configuring a neural network, comprising:
   accessing a plurality of three-dimensional (3D) emission image data sets collected by an emission scanner from respective brains of respective subjects;
   transforming each of the plurality of 3D emission image data sets to a respective two-dimensional (2D) image;
   cropping portions of each respective 2D image to remove image data corresponding to tissue outside of a striatum of each of the respective brains, to form respective cropped 2D striatum images; and
   training a neural network to detect a presence of a Parkinsonian syndrome using the cropped 2D striatum images.

2. The method of claim 1, wherein the scanner is a positron emission tomography (PET) or a single-photon emission computerized tomography (SPECT) scanner.

3. The method of claim 1, further comprising spatially normalizing the 3D emission image data sets to a standardized space before the transforming.

4. The method of claim 3, further comprising normalizing intensity of the 3D emission image data sets before the transforming.

5. The method of claim 1, wherein the 3D emission image data sets correspond to subjects injected with a dopaminergic radioligand.

6. The method of claim 1, wherein the Parkinsonian syndrome is Parkinson's disease, multiple system atrophy and progressive supranuclear palsy.

7. The method of claim 6, further comprising:
   injecting each of the subjects with a tracer targeting dopaminergic system of the subjects; and
   scanning the subjects to collect the 3D emission image data prior to the accessing step.

8. The method of claim 7, wherein the tracer comprises one of the group consisting of: [$^{123}$I]FP-CIT, [$^{123}$I]β-CIT, [$^{99m}$Tc]TRODAT-1, [$^{123}$I]PE2I, [$^{123}$I]-altropane, [$^{123}$I]IBZM, [$^{18}$F]dopa, [$^{11}$C]dopa, [$^{11}$C]cocaine [$^{3}$H]WIN, [$^{11}$C]altropane, [$^{11}$C]/[$^{18}$F]β-CFT, [$^{11}$C]FE-CIT, [$^{11}$C]dMP, [$^{11}$C]DTBZ, [$^{11}$C]raclopride, [$^{18}$F]DMFP, or [$^{11}$C]NMSP.

9. The method of claim 1, wherein each 3D image data set has a plurality of slices, each slice has a plurality of voxels, each 2D image has a plurality of pixels, and the transforming step includes averaging corresponding voxels from at least two of the slices to determine a value of a corresponding pixel of the respective 2D image.

10. The method of claim 9, further comprising determining which six consecutive slices among the plurality of slices of one of the 3D emission image data sets have highest peak distribution volume ratios,
    wherein the averaging is performed on the six consecutive slices.

11. The method of claim 10, wherein each of the plurality of slices includes a respective cross-section of the striatum of one of the brains.

12. The method of claim 1, wherein the neural network is a convolutional neural network.

13. A system for configuring a neural network, comprising:
    a processor coupled to access a plurality of three-dimensional (3D) emission image data sets collected by an emission scanner from respective brains of respective subjects;
    the processor configured to transform each of the plurality of 3D emission image data sets to a respective two-dimensional (2D) image;
    the processor configured to crop portions of each respective 2D image to remove image data corresponding to tissue outside of a striatum of each of the respective brains, to form respective cropped 2D striatum images; and
    a neural network configured to receive the cropped 2D striatum images for training the neural network to detect a presence of a Parkinsonian syndrome using the cropped 2D striatum images.

14. The system of claim 13, further comprising a positron emission tomography (PET) or a single-photon emission computerized tomography (SPECT) scanner to which the processor is coupled, for providing the plurality of 3D emission image data sets to the processor.

15. The system of claim 13, wherein the neural network is a convolutional neural network.

16. A non-transitory, machine readable storage medium encoded with program instructions, such that when a processor executes the program instructions, the program instructions configure the processor to perform a method for configuring a neural network, comprising:
    accessing a plurality of three-dimensional (3D) emission image data sets collected by an emission scanner from respective brains of respective subjects;
    transforming each of the plurality of 3D emission image data sets to a respective two-dimensional (2D) image;

cropping portions of each respective 2D image to remove image data corresponding to tissue outside of a striatum of each of the respective brains, to form respective cropped 2D striatum images; and training a neural network to detect a presence of a Parkinsonian syndrome using the cropped 2D striatum images.

17. The non-transitory, machine readable storage medium of claim 16, wherein the program instructions further configure the process for:

spatially normalizing the 3D emission image data sets to a standardized space; and normalizing intensity of the spatially normalized 3D emission image data sets.

18. The non-transitory, machine readable storage medium of claim 16, wherein each 3D image data set has a plurality of slices, each slice has a plurality of voxels, each 2D image has a plurality of pixels, and the transforming step includes averaging corresponding voxels from at least two of the slices to determine a value of a corresponding pixel of the respective 2D image.

19. The non-transitory, machine readable storage medium of claim 18, wherein the program instructions further configure the process for determining which six consecutive slices among the plurality of slices of one of the 3D emission image data sets has a have highest peak distribution volume ratios, wherein the averaging is performed on the six consecutive slices.

20. The non-transitory, machine readable storage medium of claim 16, wherein the neural network is a convolutional neural network.

* * * * *